US00PP11191P

United States Patent [19]

Riordan et al.

[11] Patent Number: Plant 11,191

[45] Date of Patent: Jan. 25, 2000

[54] BUFFALOGRASS PLANT NAMED 'NE86-120'

[75] Inventors: Terrance P. Riordan; Frederick Baxendale; Roch E. Gaussoin; Paul G. Johnson, all of Lincoln, Nebr.; Jennifer M. Johnson-Cicalese, Mt. Holly, N.J.; Edward John Kinbacher, Lincoln, Nebr.

[73] Assignee: Board of Regents University of Nebraska-Lincoln, Lincoln, Nebr.

[21] Appl. No.: 08/955,786

[22] Filed: Oct. 22, 1997

Related U.S. Application Data

[60] Provisional application No. 60/028,987, Oct. 22, 1996.

[51] Int. Cl.[7] ..... A01H 5/00

[52] U.S. Cl. ..... Plt./391

[58] Field of Search ..... Plt./90, 391

[56] References Cited

U.S. PATENT DOCUMENTS

| | | | |
|---|---|---|---|
| P.P. 7,539 | 5/1991 | Engelke et al. | Plt./391 |
| P.P. 8,475 | 11/1993 | Riordan et al. | Plt./391 |
| P.P. 8,896 | 9/1994 | Wu | Plt./391 |
| P.P. 8,897 | 9/1994 | Wu | Plt./391 |
| P.P. 9,208 | 7/1995 | Mancino | Plt./391 |
| P.P. 9,847 | 4/1997 | Riordan et al. | Plt./391 |
| P.P. 10,576 | 8/1998 | Bughrara et al. | Plt./391 |

OTHER PUBLICATIONS

Arumugathan, K. and E. D. Earle, 1991, Estimation of Nuclear DNA Content of Plants by Flow Cytometry, Plant Molecular Biology Reporter 9:229–233.

Beard, J. B. and K. S. Kim, 1989, Low–water Use Turfgrasses, USGA Green Section Record, 27:12–13.

Beetle, A. A., 1950 Buffalograss—Native of the Shortgrass Plains, Agr. Exp. Sta., Univ. of WY, Larami, Bulletin 293:1–31.

Engelke, M. C. and V. G. Lehman, 1990, Registration of Prairie Buffalograss, Crop Sci. 30:1360.

Galbraith, D. W., K. R. Harkins, J. M. Maddox, N. M. Ayres, D. P. Sharma, and E. Firoozbady, 1983, Rapid Flow Cytometric Analysis of Cell Cycle in Intact Plant Tissues, Science 220:1049–1051.

Johnson, P. G., T. P. Riordan, R. E. Gaussoin, D. J. Schwarze, and K. A. Kerner, 1997, Submitted to the Eight International Turfgass Society Research Journal.

Klingenberg, J. P., 1993, Evaluatin, Genetic Variation, and Selection for Improvement of a Seeded, Turf–Type Buffalograss Population (*Buchloë dactyloides*), Ph. D. Diss, University of Nebraska–Lincoln.

Poransky, T., 1983, Buffalograss: Home on the Range, But also A Turfgrass, Rangelands 5:214–216.

Quinn, J. A. and J. L. Engel, 1986, Life History Strategies and Sex Ratios for a Cultivar and Wild Population of *Buchloë dactyloides* (Gramineae), Am. J. of Bot. 73:874–881.

Riordan, T. P., S. A. DeShazer, J. M. Johnson–Cicalese, and R. C. Shearman, 1993, An Overview of Breeding and Development of Buffalograss for Golf Course Turf, International Turfgrass Society Research Journal 7:816–822.

Savage, D. J. and L. A. Jacobson, 1935, The Killing Effect of Heat and Drought on Buffalograss and Blue Grama Grass at Hays, Kansas, J. of American Soc. Of Agronomy 22:566–682.

Welsh, J. and M. McClelland, 1991, Fingerprinting Genomes Using PCR with Arbitrary Primers, Nucleic Acids Res. 18:7213–7218.

Wenger, L. E., 1941, Improvement of Buffalograss in Kansas, Kansas State Board of Agri. 32$^{nd}$ Biennial Report 1c 211–224.

Wenger, L. E., 1943Buffalograss, Kansas Agri. Exp. Sta. (Manhattan) Bulletin 321:1–78.

Williams, J. G. K., A. R. Kubelik, K. J. Livak, J. A. Rafalski, and S. V. Tingey, 1990, DNA Polymorphisms Amplified by Arbitrary Primers are Useful as Genetic Markers, Nucleic Acids Res. 18:6531–6535.

Wu, L. and M. A. Harivandi, 1989, Winter Turf Color Retention and Cold Resistance Among Buffalograss Collections, Proc. 6$^{th}$ Int. Turfgrass Res. Conf., pp. 137–139, I.T.S., Tokyo, Japan, H. Takatoh (ed.).

*Primary Examiner*—Howard J. Locker
*Assistant Examiner*—Ashwin Mehta
*Attorney, Agent, or Firm*—Suiter & Associates PC

[57] ABSTRACT

A vegetatively reproduced buffalograss cultivar named 'NE86-120' is distinguished from other commercially produced buffalograss varieties by its excellent turfgrass color, cold tolerance, high density, dark green color, low growth habit, and rate of establishment. 'NE86-120' is also distinguished from other varieties by molecular markers and nuclear DNA content. 'NE86-120' is suitable for use in low to medium maintenance situations in arid and semi-arid climates of United States and Canada.

3 Drawing Sheets

CROSS-REFERENCE TO RELATED APPLICATIONS

This application claims priority under 35 U.S.C. § 119(e) to U.S. provisional application Ser. No. 60/028,987, filed Oct. 22, 1996.

This application is also related to U.S. provisional application Ser. No. 60/028,988, filed Oct. 22, 1996, and U.S. provisional application Ser. No. 60/028,749, filed Oct. 23, 1996, both hereby incorporated by reference in their entireties.

This application is also related to U.S. application Ser. No 08/956,070 and U.S. application Ser. No. 08/969,526, both filed on even date herewith, both hereby incorporated by reference in their entireties.

BACKGROUND OF THE INVENTION

Buffalograss [*Buchloë dactyloides* (Nutt) Engelm.] is a perennial, low growing, dioecious, warm-season grass species native to the Great Plains of North America. It thrives in semi-arid conditions, even under heavy grazing pressure, and spreads by branching stolons, creating a dense sod (Wenger, 1943; Beetle, 1950; Huff & Wu, 1987). Because of this adaptation, buffalograss can withstand combinations of cold, heat, and drought stress, yet still maintain an attractive turf (Wenger, 1943).

The center of origin for buffalograss is most likely central Mexico (Quinn & Engel, 1986; Shaw et al., 1987). It is native to an area from central Mexico to southern Canada (Wenger, 1943; Beetle, 1950) and altitudes below 2000 meters (Beetle, 1950). The range of adaptation is relatively stable, however seasonal precipitation variation may alter the eastern boundary (Wenger, 1941; 1943; Beetle, 1950). Buffalograss is the dominant species in the short grass prairie and cannot compete with the taller grasses in prairie communities in higher rainfall areas (Poransky, 1983).

Buffalograss was threatened with extinction due to heavy grazing and agricultural production (Beetle, 1950), but during the 1930's, it was recognized for its usefulness in restoring plant cover in the Great Plains after extreme drought, to prevent wind and water erosion of the soil. The drought resistance of buffalograss has been shown, in part due to its low evapotranspiration rate of six mm per day under optimum growth conditions. This is less than any other commonly used warm and cool-season turfgrass. Characteristics responsible for the drought resistance include a finely branched root system, low growth habit, and the ability of leaf blades to limit transpiration by rolling longitudinally during drought stress (Savage & Jacobsen, 1935; Engleke & Hickey, 1983). Buffalograss will go dormant sooner than other grasses and will resume growth quickly once favorable moisture returns (Savage & Jacobsen, 1935; Beetle, 1950). Buffalograss survived mowing heights under 2.5 inches better than other native species with a noticeable increase in horizontal spreading and improved weed competition. These drought resistant and mowing tolerant characteristics make buffalograss a useful turfgrass in semi-arid portions of North America.

Buffalograss can be established by two methods: vegetative propagation or seed (Wenger, 1943; Poransky, 1983). Buffalograss establishment has typically been expensive. Vegetative propagation of buffalograss plugs or sod pieces has traditionally been done because low seed production of native stands and poor seedling establishment. Developments of automated pluggers and "big roll" sod handlers (Riordan et al., 1993) have made vegetative propagation more economical. Improvements have also been made in seed production and seed treatments (Klingenberg, 1993).

Buffalograss has been used for many years on highway shoulders or right-of-ways, airfield runways, cemeteries, parks, golf courses, and other athletic fields (Wenger, 1943; Beetle, 1950; Poransky, 1983). Because of environmental concerns and changes in landscape priorities, buffalograss has tremendous potential as a turfgrass. Breeding and development efforts are relatively new with emphasis on developing turf-type buffalograss cultivars which have low growth habit, improved color, faster establishment, improved density, extended growing season, and recuperative potential (Riordan et al., 1993; Engelke & Lehman, 1990; Wu & Harivandi, 1991).

SUMMARY OF THE INVENTION

'NE86-120' is distinguished from other commercially available buffalograss cultivars. It is a vegetatively propagated female clone with darker green foliage and lower growth habit than 'Prairie' (U.S. Plant Pat. No. 7,539) '609' (U.S. Plant Pat. 8,745), and '315' (U.S. Plant Pat. No. 9,847) buffalograsses and is brighter green than 'NE86-61'. 'NE86-120' also exhibits better overall turfgrass quality, density, and uniformity than seeded buffalograss varieties. It is best adapted to central and northern parts of the Great Plains. 'NE86-120' provides an attractive turf which requires less water, fertilizer, and mowing than other turfgrass species. These characteristics, along with field and greenhouse evaluations have shown 'NE86-120' is well adapted to golf course roughs, home lawns, and general use areas requiring reduced management inputs.

BRIEF DESCRIPTION OF THE ILLUSTRATIONS

DETAILED DESCRIPTION OF THE PLANT

Buffalograss 'NE86-120' was found in a mowed and maintained (cultivated) cemetery, off of Highway 24 in Osborne County, Kans. After being collected, it was vegetatively (asexually) propagated. This is the way all buffalograsses are handled if they are being clonally propagated. In particular, buffalograss 'NE86-120' was propagated vegetatively (asexually) at the John Seaton Anderson Turfgrass Research Facility near Mead, Nebr. Plugs and stolons were used to propagate it. The cultivar is completely stably reproduced by the aforementioned means. This selection, along with several thousand other selections, was evaluated at the John Seaton Anderson Turfgrass Research Facility near Mead, Nebr. The growth characteristics, turfgrass evaluation ratings, and molecular markers can be used to distinguish 'NE86-120' from other commerically produced buffalograss varieties.

Morphological Characteristics

Figure 1:
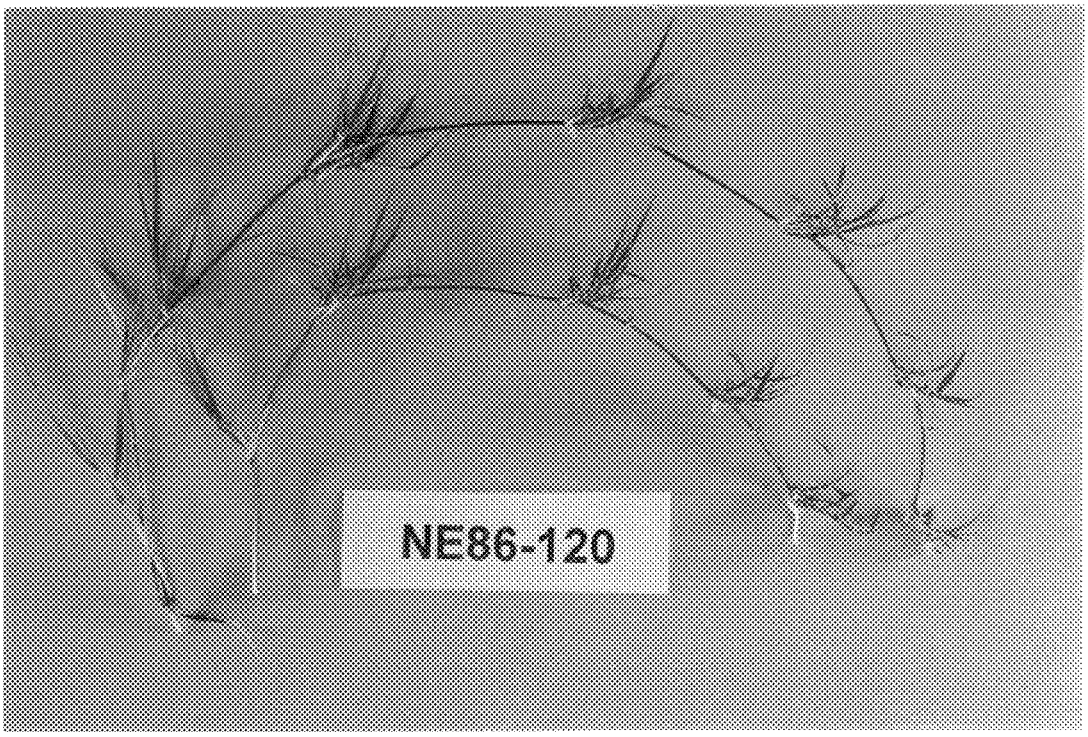
FIG. 1 is a photograph of a typical stolon of 'NE86-120'.

Buffalograss 'NE86-120' has larger stolon internodes (internodes 2 and 3 ) than '315' and 'NE 91-118' (Table 1). We did not feel that 'NE86-120' stolon internode length was significantly different from '609,' 'NE86-61', or 'Texoka,' based on standard deviations (Table 1). For third internodes width, 'NE86-120' has an internode width smaller than 'Texoka,' similar to '315' and '609,' and larger than 'NE86-61' and 'NE91-118' (Table 1). See also FIG. 1, depicting a typical stolon of 'NE 86-120'. Leaf width measurements are smaller than 'Texoka' (Table 2), indicating finer texture of the resulting turf. Pubescent nodes (Table 1) and leaves (Table 4) are two of the most distinguishing characteristic of 'NE86-120'. The purpose or adaptation of pubescence on buffalograss is not known, but may decrease evaporation of water from leaf surfaces (Kramer, 1983). The female flowers (burs) tend to be larger than the other varieties (Table 3).

Turfgrass Characteristics

Figure 2:
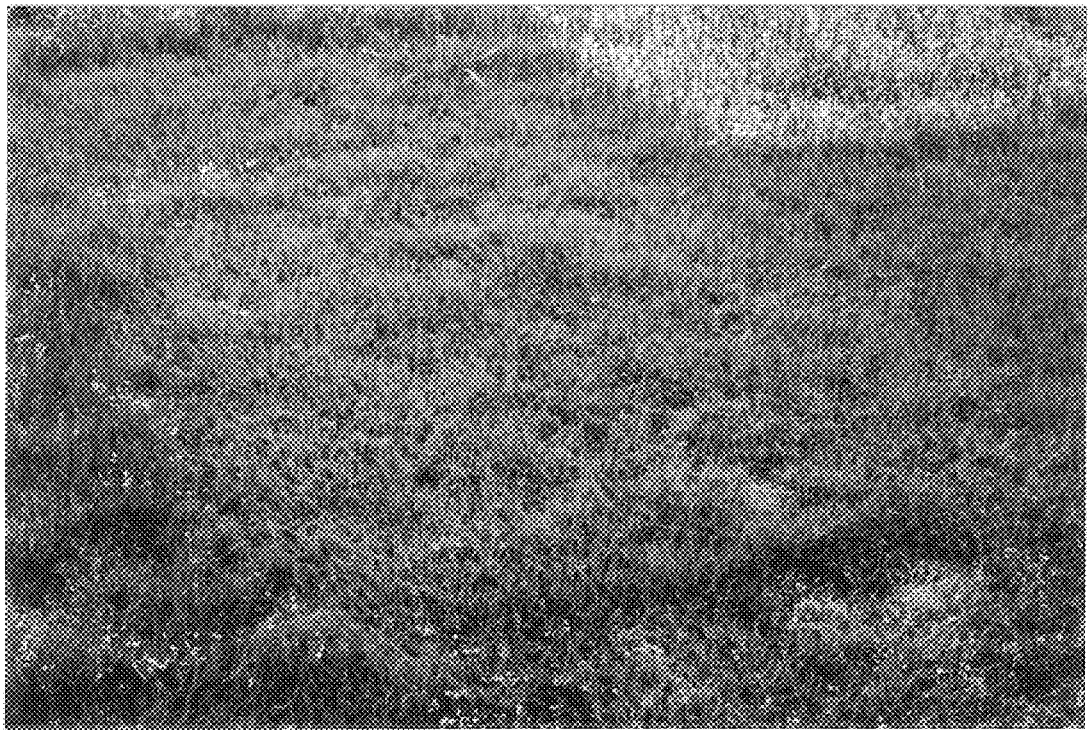
FIG. 2 is a photograph of turf produced by 'NE86-120', taken at Mead, NE.
Figure 3:
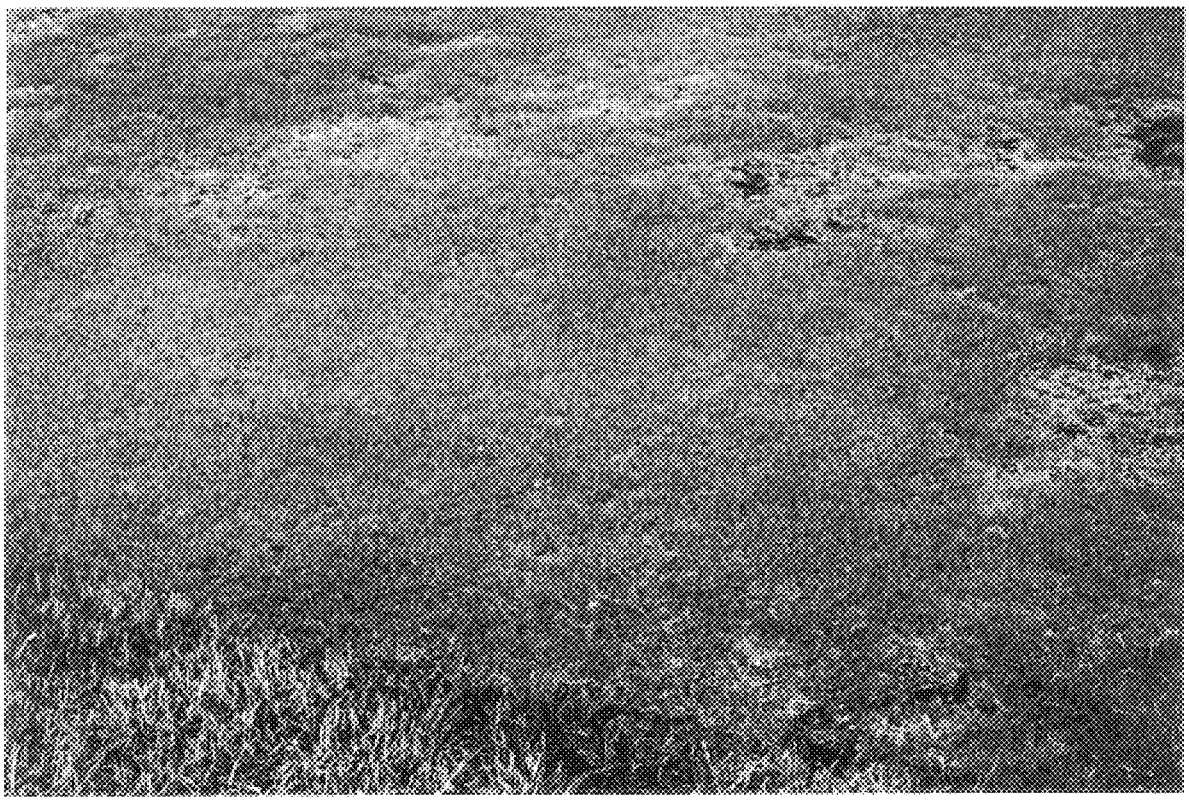
FIG. 3 is a photograph of 'NE86-120', at Mead, NE, exhibiting good turf quality when mowed at 5/8".

A quality turfgrass stand must have good, pleasing color. 'NE86-120' consistently produces dark green turf, which is favored by most consumers (FIGS. 2 & 3). Turfgrass color ratings of 'NE86-120' are higher in greenhouse evaluations, compared to '315,' '609,' and 'Texoka,' and similar to 'NE86-61' (Table 5), but not with the grayish hue of 'NE86-61'. 'NE-86-120' also exhibited higher ratings in field evaluations (Tables 6 & 7).

Turfgrass quality is a combination of several factors: density, texture, uniformity, and color (Turgeon, 1980). 'NE86-120' has improved quality compared to older, forage type buffalograsses such as 'Texoka,' but also improved quality compared to turf varieties '315,' '378,' '609,' and 'Prairie' (Tables 6 & 7). 'NE86-120' exhibited superior quality when mowed at heights down to ⅝", similar to the height used on golf course fairways (Table 6). Lower growth habit and denser canopy contribute to its tolerance to low mowing.

Buffalograss 'NE86-120' cannot at this time be distinguished from other buffalograss based on the characteristics of heat, drought, or salinity tolerance. Buffalograss has better heat and drought tolerance than other turfgrass species, but less salinity tolerance.

Buffalograss 'NE86-120' has canopy density and inflorescence characteristics that are not distinguishable from other buffalograsses, with the exception of, perhaps, 'Texoka.' Buffalograss canopy density and inflorescence characteristics would be different than for other species.

All northern adapted plants survive the winter cold period by going dormant early in fall and resume growth in the spring (Riordan et al., 1993). 'NE86-120' is a typical northern-adapted cultivar in this respect. Southern adapted cultivars, such as '609' and 'Prairie,' remain actively growing late into the fall, resulting in higher quality ratings (Tables 6 & 7) but are subject to winterkill during Nebraska winters.

Molecular Marker Analysis

DNA fingerprinting was conducted using polymerase chain reaction (PCR) (Welsh and McClelland, 1991; Williams et al., 1990). DNA profiles of 'NE86-120' were compared with '315,' '378,' 'NE84-45-3', '609,' 'NE86-61', 'NE91-118', and bulked sample of 'Texoka' progeny. DNA was extracted from fresh leaf tissue using 'Easy-DNA™ Kit' from Invitrogen (San Diego, Calif.). Fresh leaf tissue from each clone was ground with a mortar and pestel with liquid nitrogen. For 'Texoka,' leaf tissue was collected from three solid seeded pots and bulked to obtain a bulked DNA sample from this seeded cultivar.

PCR was performed using decamer primers OPA-07 and OPA-16 from Operon Technologies (Alameda, Calif.). Samples were separated on a polyacrylamide gel and DNA fragments were visualized using ethidium bromide staining. DNA amplification was performed using an Idaho Technologies thermocycler (Idaho Falls, Id.) with two cycles of denaturing at 94° C. for one minute, annealling at 40° C. for seven seconds, and extension at 72° C. for 70 seconds, followed by 43 cycles of denaturing at 94° C. for three seconds, annealing at 40° C. for seven seconds, extension at 72° C. for 70 seconds. PCR reactions were performed in a volume of 25 μl. The PCR reaction components were as follows:

| Component | Volume | Concentration |
|---|---|---|
| Sterile $H_2O$ | 12.5 μl | |
| 10X buffer | 2.5 μl | |
| Tris | | 50 mM, pH 8.3 |

-continued

| Component | Volume | Concentration |
|---|---|---|
| Bovine Serum Albumin | | 5 mg/ml |
| MgCl | | 25 mM |
| Sucrose | | 40% (w/v) |
| Cresol Red | | 1 mM |
| dNTPs | 2.5 μl | 2 mM each dNTP |
| Taq DNA polymerase | 2.5 μl | 0.4 U/μl |
| Primer | 2.5 μl | 5 μM |
| DNA | 2.5 μl | 25 ng/μl |

Primers used for DNA fingerprinting were OPA-07 and OPA-16 from Operon Technologies. Samples were loaded in a 5% polyacrylamide gel and electrophoresed at 44 volts (24 milliamps) in a TBE-8 buffer for approximately 2 hours and 45 minutes. DNA was visualized in the gel using ethidium bromide staining.

Figure 4:
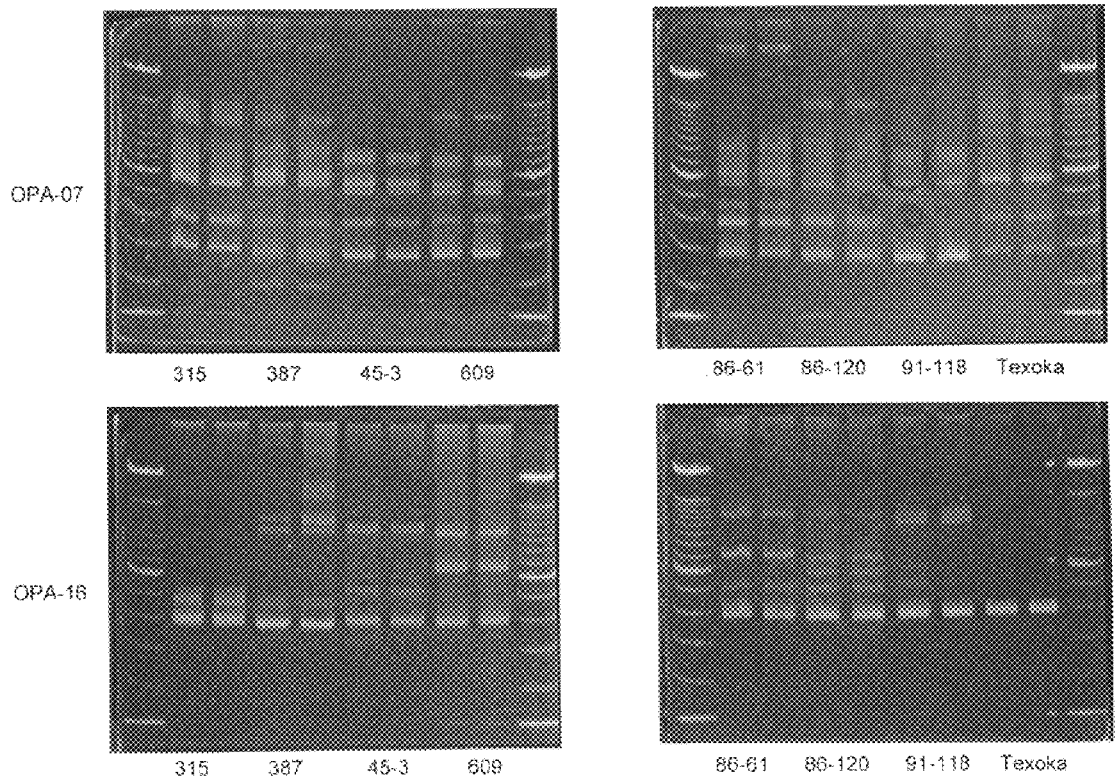
FIG. 4 depicts DNA fingerprints of selected buffalograss varieties.

The DNA profiles produced are shown in FIG. 4. Using primer OPA-07, 'NE-86-120' was the only genotype with a band of 1700 base-pairs (bp). With primer OPA-16, 'NE86-120' was the only genotype with a band at >2020 bp.

Flow Cytometric Analysis

Flow cytometry was used to measure the nuclear DNA content within buffalograss cells. This method is a rapid way to differentiate between varieties having different numbers of chromosomes, and sometimes can differentiate among varieties having the same number of chromosomes. The detailed protocol for this method is listed below.

1. Collect young buffalograss leaves and keep moist at 4° C.

2. Place 25–30 mg of the buffalograss leaves and 25–30 mg of *Poa annua* (UM-184) leaves in a petri dish on ice. DNA content of UM-184 *Poa annua* was determined separately and repeatedly as 4.64 picograms of DNA/nucleus.

3. Add with 1.0 ml of ice-cold buffer-propidium iodide solution and chop leaves into thin strips (<0.5 mm) with a scalpel. 15 ml of buffer solution, enough for 12–13 samples contains 14.3 ml of $MgSO_4$ buffer solution (1OmM $MgSO_4 \cdot 7H_2O$,50mM KCl, 5mM Hepes), 15 mg dithiothreitol, 300 μl propidium iodide stock (5 mg/ml), 375 μl Triton X-100 stock (10% w/v).

4. Filter the slurry through 30 μm nylon mesh.

5. Centrifuge at 15,000 rpm for 15 seconds. Discard supernatant.

6. Resuspend in 200 μl propidium iodide buffer solution + RNAse. (3 ml of extraction solution and 7.5 μl of DNAase free RNAase.)

7. Incubate sample for 15 min. at 37° C.

8. Analyze on a Becton-Dickson FACScan flow cytometer using a wavelength of 488 nm (FIG. 1).

9. Calculate DNA content of buffalograss sample.

$$= \frac{\text{mean of buffalograss peak}}{\text{mean of } \textit{Poa annua} \text{ peak}} \times \text{DNA content of } \textit{Poa annua} \text{ (4.64 pg/nucleus)}$$

Intact cell nuclei were isolated from young buffalograss leaves and passed through a flow cytometer to measure the amount of DNA in each nucleus. 'NE86-120' was determined to have 2.59±0.04 picograms DNA per nucleus (Table 8). This places 'NE 86-120' in the hexaploid group of buffalograsses together with '378' and 'NE86-61' having 60 chromosomes. 'Stampede' is a diploid having 20 chromosomes and 'Prairie,' '609,' and 'NE91-118' are tetraploid having 40 chromosomes. '315' is a pentaploid having 50 chromosomes (Table 8).

Comparitive Data

The following tables provide data comparison of 'NE86-120,' '315,' '378,' '609,' 'NE86-61', 'NE91-118', 'Texoka,' and 'Prairie.'

TABLE 1

Internodal and nodal characteristics of buffalograsses (University of Nebraska Greenhouse, Winter, 1996–97).

| | Internode Length[1] | | Third Internode | Node |
|---|---|---|---|---|
| Selection | Internode 2 (mm) | Internode 3 (mm) | Width[1] (cm) | Pubescence[2] (1–9) |
| 'NE 86-120' | 5.3 ± 0.1 | 6.2 ± 0.4 | 3.9 ± 0.5 | 8.9 ± 0.1 |
| 'NE 91-118' | 4.2 ± 0.3 | 4.4 ± 0.4 | 3.0 ± 0.4 | 1.2 ± 0.1 |
| 'NE 86-61' | 5.0 ± 1.5 | 4.7 ± 0.9 | 2.8 ± 0.4 | 6.2 ± 0.1 |
| '315' | 3.9 ± 0.6 | 3.7 ± 0.2 | 3.7 ± 0.4 | 5.7 ± 0.6 |
| '609' | 5.6 ± 0.1 | 6.0 ± 0.2 | 3.6 ± 0.4 | 1.0 ± 0.0 |
| 'Texoka' | 6.1 ± 1.3 | 6.2 ± 2.0 | 4.9 ± 0.2 | 4.2 ± 0.8 |

[1]Average of five measurements on each of three replications.
[2]Qualitative scale for trichome density, 1 = none, 5 = moderate, 9 = heavy or fuzzy

TABLE 2

Leaf length and width measurements of buffalograsses (University of Nebraska Greenhouse, Winter, 1996–97).

| Selection | Leaf blade Length[1] (mm) | Leaf blade Width[1] (mm) |
|---|---|---|
| 'NE 86-120' | 163.5 ± 25.2 | 1.5 ± 0.1 |
| 'NE 86-61' | 120.7 ± 1.8 | 1.6 ± 0.1 |
| 'NE 91-118' | 111.7 ± 6.4 | 1.4 ± 0.2 |
| '315' | 120.2 ± 9.2 | 1.6 ± 0.1 |
| '609' | 123.5 ± 5.1 | 1.4 ± 0.1 |
| 'Texoka' | 198.9 ± 10.5 | 2.0 ± 0.1 |

[1]Average of five measurements on each of three replications.

TABLE 3

Bur length and width measurements of buffalograsses (University of Nebraska Greenhouse, Winter, 1996–97).

| Selection | Bur Length[1] (mm) | Bur Width[1] (mm) |
|---|---|---|
| 'NE 86-120' | 7.8 ± 0.6 | 2.8 ± 0.0 |
| 'NE 86-61' | 7.0 ± 0.2 | 2.8 ± 0.7 |
| '315' | 7.2 ± 0.2 | 2.5 ± 0.0 |
| '609' | 6.6 ± 0.2 | 3.0 ± 0.6 |
| 'Texoka' | 7.3 ± 0.7 | 2.9 ± 0.4 |

[1]Average of up to five measurements on each of three replications.

TABLE 4

Leaf pubsecence ratings of buffalograsses (University of Nebraska Greenhouse, Winter, 1996–97).

| Selection | Leaf Pubsecence[1] (1–9) |
|---|---|
| 'NE 86-120' | 7.7 ± 0.2 |
| 'NE 86-61' | 7.8 ± 0.1 |

TABLE 4-continued

Leaf pubsecence ratings of buffalograsses (University of Nebraska Greenhouse, Winter, 1996–97).

| Selection | Leaf Pubsecence[1] (1–9) |
|---|---|
| 'NE 91-118' | 5.7 ± 0.4 |
| '315' | 5.5 ± 0.2 |
| '609' | 1.0 ± 0.0 |
| 'Texoka' | 6.1 ± 0.4 |

[1]Qualitative scale for trichrome density, 1 = none, 5 = moderate, 9 = heavy or fuzzy.

TABLE 5

Genetic color ratings of buffalograsses (University of Nebraska Greenhouse, Winter, 1996–97).

| Selection | Genetic Color[1] (1–9) | Leaf Color[2] |
|---|---|---|
| 'NE 86-120' | 6.7 ± 0.9 | 137-A |
| 'NE 86-61' | 7.8 ± 0.2 | 137-A |
| 'NE 91-118' | 5.7 ± 0.4 | 137-C |
| '315' | 6.2 ± 0.2 | 137-C |
| '609' | 5.8 ± 0.2 | 137-C |
| 'Texoka' | 5.7 ± 0.7 | 137-C |

[1]Qualitative scale for plant color, 1 = yellow, 5 = medium green, 9 = dark green to bluegreen.
[2]According to the R.H.S. Colour Chart in association with the Flower Council of Holland; 137-A is darker than 137-C.

TABLE 6

Turfgrass quality, color, and fall dormancy ratings, 1992–96[1] (Area 16, University of Nebraska John Seaton Anderson Turfgrass Research Facility, Ithaca, NE).

| Selection | Turfgrass Quality[2] (1–9) | Turfgrass Color[3] (1–9) | Fall Dormancy[4] (1–9) |
|---|---|---|---|
| 'NE 86-120' | 6.7 | 6.3 | 3.9 |
| 'NE 86-61' | 7.0 | 7.1 | 4.0 |
| '315' | 6.4 | 5.8 | 3.9 |
| '609' | 4.5 | 5.7 | 6.7 |
| 'Prairie' | 3.8 | 4.9 | 6.9 |
| 'Texoka' | 4.6 | 5.4 | 4.9 |
| LSD (.05) | 0.7 | 0.7 | 1.4 |

[1]Field plot was mowed at 2.5 inches during 1992 and 1993, at ⅝" during 1994–1996.
[2]Qualitative scale for overall quality, 1 = dead, 5 = acceptable quality, 9 = ideal turf quality.
[3]Qualitative scale for plant color, 1 = yellow, 5 = medium green, 9 = dark green to bluegreen.
[4]Qualitative rating of late fall growth, 1 = completely dormant, no green leaves visible, 5 = approx. 50% green leaves visible, 9 = no dormancy observed, all green leaves.

TABLE 7

Turfgrass quality, color, and fall dormancy ratings, 1994–96 (Area 17, University of Nebraska John Seaton Anderson Turfgrass Research Facility, Ithaca, NE).

| Selection | Turfgrass Quality[1] (1–9) | Turfgrass Color[2] (1–9) | Fall Dormancy[3] (1–9) |
|---|---|---|---|
| 'NE 86-120' | 6.3 | 6.3 | 2.8 |
| 'NE 86-61' | 6.6 | 6.2 | 5.6 |
| 'NE 91-118' | 5.8 | 5.3 | 5.3 |
| '315' | 6.1 | 5.8 | 4.9 |
| '378' | 6.0 | 6.1 | 3.4 |

TABLE 7-continued

Turfgrass quality, color, and fall dormancy ratings, 1994–96 (Area 17, University of Nebraska John Seaton Anderson Turfgrass Research Facility, Ithaca, NE).

| Selection | Turfgrass Quality[1] (1–9) | Turfgrass Color[2] (1–9) | Fall Dormancy[3] (1–9) |
|---|---|---|---|
| 'Texoka' | 4.9 | 4.8 | 4.2 |
| LSD (.05) | 1.0 | 1.1 | 2.4 |

[1]Qualitative scale for overall quality, 1 = dead, 5 = acceptable quality, 9 = ideal turf quality.
[2]Qualitative scale for plant color, 1 = yellow, 5 = medium green, 9 = dark green to bluegreen.
[3]Qualitative rating of late fall growth, 1 = completely dormant, no green leaves visible, 5 = approx. 50% green leaves visible, 9 = no dormancy observed, all green leaves.

TABLE 8

DNA contents of buffalograss clones.

| Family name | n | DNA Content (pg/nucleus) | SE (pg/nucleus) |
|---|---|---|---|
| Diploid[1] | | | |
| 'Stampede' | 7 | 0.93 | 0.01 |
| Tetraploid[2] | | | |
| 'Prairie' | 2 | 1.80 | 0.00 |
| 'NE-91-118' | 10 | 1.81 | 0.02 |
| '609' | 9 | 1.81 | 0.02 |
| Pentaploid[3] | | | |
| '315' | 11 | 2.29 | 0.02 |
| Hexaploid[4] | | | |
| 'NE 86-120' | 24 | 2.59 | 0.04 |
| 'NE 86-61' | 8 | 2.58 | 0.02 |
| '378' | 7 | 2.60 | 0.09 |

[1]2n = 20
[2]2n = 40
[3]2n = 50
[4]2n = 60

THE VARIETY

Origin: Plant selected from a mowed, managed cemetery, off Highway 24 in Osborne County Kans.

Classification:

*Botanic.*—*Buchloë dactyloides* (Nutt.) Engelm.

Chromosome number: 2n=6x=60.

Form: Monocot Gramineae.

Growth habit: A perennial plant, with a stoloniferous growth habit, which allows it to be propagated vegetatively. It will spread slowly under non-competitive conditions and when conditions favor stolon growth. It has a very fibrous root system which can have a depth of 100 to 150 cm. It will produce a dense, fine-textured turf with dark green color throughout most of the growing season. From middle fall to early spring, the grass is dormant.

Establishment rate:

*Plugs.*—12–14 weeks with irrigation.

*Sod.*—1–2 weeks.

*Sprigs.*—Not recommended.

Regions of adaptation: North to south, from the U.S.-Canada border to northern Mexico, east to west, from Missouri to California. The exact geographic region of adapation is currently under investigation in a national test directed by the National Turfgrass Evaluation Program.

Blade:[1]

*Shape.*—Long, slender.

*Length.*—16 cm.

*Width.*—1.5 mm.

*Pubescence.*—Heavy, compared to other buffalograsses.

Leaf color:2 Dark green, 137-A.

Mature plant height: 15 cm.

Above canopy stolons: Minimal compared to 'Prairie.'

Internode length:[1] 5 cm (internode 2).

Internode color:[1,2] Yellow-green, 146-B.

Node width:[1] 2.8 mm (node 3).

Soil adaptation:

*Heavy soils.*—Silty clay loam preferred, slightly acid to alkaline pH.

Female inflorescence: Present, heavy in early growing season. The inflorescence is a spike.

Male inflorescence: Absent.

[1] Measurements made on greenhouse grown plants.
[2] RHA Colour Chart Designations.

REFERENCES

All references cited herein are hereby incorporated by reference in their entireties.

Arumuganathan, K. and E.D. Earle, 1991. Estimation of nuclear DNA content of plants by flow cytometry. Plant Molecular Biology Reporter 9:229–233.

Beard, J.B. and K.S. Kim, 1989. Low-water use turfgrasses. USGA Green Section Record. 27:12–13.

Beetle, A.A., 1950. Buffalograss—native of the shortgrass plains. Agr. Exp. Sta., Univ. of WY, Laramie. Bulletin 293:1–31.

Engelke, M.C. and V.G. Hickey, 1983. Buffalograss germplasm diversity and development for semi-arid turf. Texas Turfgrass Proc. PR 4150. pg. 21–22.

Engelke, M.C. and V.G. Lehman, 1990. Registration of Prairie buffalograss. Crop Sci. 30:1360.

Galbraith, D.W., K.R. Harkins, J.M. Maddox, N.M Ayres, D.P. Sharma, and E. Firoozbady, 1983. Rapid flow cytometric analysis of cell cycle in intact plant tissues. Science 220:1049–1051.

Givan, A.L., 1992. Flow Cytometry: first principles. Wiley-Liss, Inc. New York, N.Y.

Johnson, P.G., T.P. Riordan, R.E. Gaussoin, D.J. Schwarze, and K.A. Kerner, 1997. Submitted to the Eight International Turfgrass Society Research Journal.

Klingenberg, J.P., 1993. Evaluatin, genetic variation, and selection for improvment of a seeded, turf-type buffalograss population (*Buchloë dactyloides*). Ph.D. diss. Unversity of Nebraska-Lincoln.

Kramer, P.J., 1983. Water Relations of Plants. Academic Press. New York, N.Y.

Poransky, T. 1983. Buffalograss: Home on the range, but also a turfgrass. Rangelands 5:214–216.

Quinn, J.A. and J.L. Engel, 1986. Life history strategies and sex ratios for a cultivar and wild population of *Buchloë dactyloides* (Gramineae). Am. J. of Bot. 73:874–881.

RHS Colour Chart, 1966. The Royal Horticultural Society. London.

Riordan, T.P., S.A. deShazer, J.M. Johnson-Cicalese, and R.C. Shearman, 1993. An overview of breeding and development of buffalograss for golf course turf. International Turfgrass Society Research Journal 7:816–822.

Savage, D.J. and L.A. Jacobson, 1935. The killing effect of heat and drought on buffalograss and blue grama grass at Hays, Kans. J. of American Soc. of Agronomy 22:566–682.

Turgeon, A.J., 1980. Turfgrass Management. Reston Publishing Co., Inc. Reston, Va. 22090.

Welsh, J. and M. McClelland, 1991 .Fingerprinting genomes using PCR with arbitrary primers. Nucleic Acids Res. 18:7213–7218.

Wenger, L.E., 1941. Improvement of buffalograss in Kansas. Kansas State Board of Agri. 32nd Biennial Report. 1c 211–224.

Wenger, L.E., 1943. Buffalograss. Kansas Agri. Exp. Sta. (Manhattan) Bulletin 321:1–78.

Williams, J.G.K., A.R. Kubelik, K.J. Livak, J.A. Rafalski, and S.V. Tingey, 1990. DNA polymorphisms amplified by arbitrary primers are useful as genetic markers. Nucleic Acids Res. 18:6531–6535.

Wu, L. and M.A. Harivandi, 1989. Winter turf color retention and cold resistance among buffalograss collections. Proc. 6th Int. Turfgrass Res. Conf. pp. 137–139. I.T.S., Tokyo, Japan. H. Takatoh (ed.).

What is claimed is:

1. A new and distinct perennial, female buffalograss cultivar, substantially as herein shown and described, distinguished by its dark green color, improved turfgrass quality, tolerance to low moving, unique molecular marker pattern, hexaploid DNA content, vegetative propagation, and tolerance to heat, drought, cold, and low maintenance conditions.

* * * * *